United States Patent [19]

Chambers et al.

[11] 4,254,290

[45] Mar. 3, 1981

[54] ACIDIC MIXED OXIDE CATALYTIC DE-ALKYLATION OF TERTIARY-ALKYL-ETHER-ALKANOLS

[75] Inventors: Gregory R. Chambers, Rexford; William E. Smith, Schenectady, both of N.Y.

[73] Assignee: General Electric Company, Schenectady, N.Y.

[21] Appl. No.: 105,577

[22] Filed: Dec. 20, 1979

[51] Int. Cl.$^3$ ............................................. C07C 31/18
[52] U.S. Cl. .................................................. 568/866
[58] Field of Search ........................................ 568/866

[56] References Cited

FOREIGN PATENT DOCUMENTS 824551 12/1959 United Kingdom ...................... 568/866

Primary Examiner—Paul J. Killos
Attorney, Agent, or Firm—F. Wesley Turner; James C. Davis, Jr.; Joseph T. Cohen

[57] ABSTRACT

A de-alkylation process which comprises contacting a t-alkylether-alkanol, e.g. 4-t-butylether-n-butan-1-ol, with an acidic solid mixed oxide, e.g. silica-alumina, catalyst which results in the formation of alkanediols, e.g. 1,4-butanediol, in the substantial absence of undesirable side reactions, e.g. the formation of tetrahydrofuran. The resulting alkanediols are useful in the preparation of polyesters, e.g. polybutylene terephthalates.

10 Claims, No Drawings

ACIDIC MIXED OXIDE CATALYTIC DE-ALKYLATION OF TERTIARY-ALKYL-ETHER-ALKANOLS

CROSS-REFERENCE TO RELATED APPLICATIONS

This invention is related to W. E. Smith's U.S. Application Ser. No. 189,190 filed Sept. 22, 1980, a continuation-in-part of U.S. Ser. No. 105,876, filed Dec. 20, 1979, now abandoned, which describes the use of an acidic zinc halide catalyst in a t-alkylether-alkanol de-alkylation process.

BACKGROUND OF THE INVENTION

1. Field of the Invention

This invention relates to the use of a solid acidic mixed oxide catalyst to enhance a process which converts t-alkylether-alkanols to alkanediols in the substantial absence of undesirable cyclic ether by-products.

2. Description of the Prior Art

The de-alkylation of certain t-alkylether-alkanols such as 4-t-butylether-n-butan-1-ol to form alkanediols, such as 1,4-butanediol employing acidic catalysts, such as aqueous phosphoric acid or sulfuric acid, as well as acid ion exchange resins at temperatures of about 100° C. has been reported.

The dehydration of certain alkanediols such as 1,4-butanediol to form cyclic ethers, such as tetrahydrofuran employing strong acid catalysts such as phosphoric acid, acidic clays, acidic alumina at temperatures of about 120° C. has also been reported.

DESCRIPTION OF THE INVENTION

The process of this invention comprises contacting a solid acidic mixed oxide catalyst and a 4-t-alkylether-alkan-1-ol to selectively form alkan-1,4-diols in the substantial absence of cyclic ethers.

The t-alkylether-alkanols are defined by the formula:

$$\begin{array}{c} R_1 \\ | \\ R_2-C-O-CH_2-CH_2-CH_2-CH_2OH \\ | \\ R_3-CH \\ | \\ R_4 \end{array} \quad (I)$$

wherein $R_1$ and $R_2$ each, independently of the other, represents a $C_1$ to $C_4$ alkyl radical, and $R_3$ and $R_4$ each, independently of the other, represents a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $C_4$ represents a hydrogen atom or a $C_1$ to $C_3$ alkyl radical.

The reaction conditions of this process promote the formation ($k_1$) of alkanediols and alkenes while limiting the formation of cyclic ethers, i.e. ($k_2$).

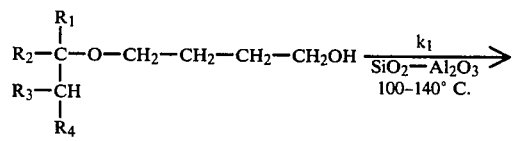

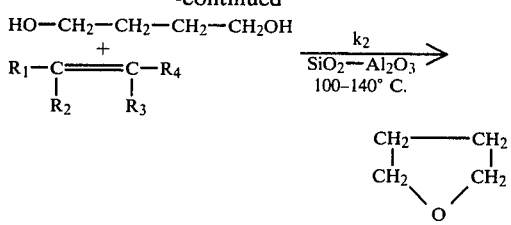

wherein $R_1$, $R_2$, $R_3$ and $R_4$ are the same as defined herein before.

The solid acidic mixed oxide catalysts include any solid acidic silica-alumina composition, e.g. any solid acidic oxide mixture of silica and alumina, i.e. $SiO_2 \cdot Al_2O_3$. The oxides of silica and alumina can be present in any proportion. Illustratively, the weight percent of presently preferred $SiO_2 \cdot Al_2O_3$ mixed oxides are within the range of from about 90:10 to about 70:30.

Surface area parameters of the mixed oxides measured in square meters per gram ($m^2/g$) are not critical to the efficacy of the process. Generally effective $SiO_2 \cdot Al_2O_3$ surface areas are within the range of from about 50 to about 400 $m^2/g$.

Temperature parameters relative to optimum conversion of t-alkylether-alkanol to alkanediol without the formation of cyclic ethers are temperatures within the range of from about 100°–140°, preferably from about 125° to 135° C.

Pressure parameters are not critical to the efficacy of the process. Accordingly the process can be carried out under widely varying pressures, e.g. sub-, super- or atmospheric pressures.

In a presently preferred embodiment of this process where 4-t-butylether-n-butan-1-ol is de-alkylated to form 1,4-butanediol at least 60, preferably about 75–80, mole percent of 4-t-butylether-n-butan-1-ol is de-alkylated to form 1,4-butanediol while the minimum ultimate selectivity of the process provides a butanediol-tetrahydrofuran product selectivity (Sel.) of at least about 95 percent based upon the following calculation.

$$\text{Sel.} \geq 95\% = \frac{\text{(moles of butanediol product)}}{\text{(moles of butanediol product + moles of tetrahydrofuran by-product)}} \times 100$$

Examples I–IV illustrate the best mode of practicing this invention.

FIRST GENERAL PROCEDURE

A series of de-alkylation reactions were carried out involving the conversion of 4-t-butylether-n-butan-1-ol to 1,4butanediol using a solid acidic $SiO_2 \cdot Al_2O_3$ catalyst. 4.0 Grams 98+% of 4-t-butylether-n-butan-1-ol and 0.2 grams of $SiO_2 \cdot Al_2O_3$ blanketed with $N_2$ were heated in a 25 ml flask fitted with a reflux condenser and a magnetic stirrer. The evolved gas isobutylene containing some entrained THF and/or t-butanol, escaping from the reflux condenser was collected at $-78°$ C. and quantified by standard vacuum line techniques at the conclusion of the reaction.

The liquid phase reaction product constituents were monitored employing standard G.P.C. techniques throughout the course of the reactions. The mass balance of liquid and gasous products of Examples I–IV was within the range of from 95-99%. A summary of the liquid phase reaction medium constitutes, e.g. tetrahydrofuran (THF), t-butanol, 1,4-di-t-butoxybutane, 4-t-butylether-n-butan-1-ol, and 1,4-butanediol correlated with elapsed reaction time period is reported in Tables I–IV.

1,4-butanediol using other acidic candidates, e.g. $SiO_2$, $Al_2O_3$, $MgO$, $WO_3 \cdot Al_2O_3$, Acidic Clay, Acid Ion Exchange Resin, and Aqueous $H_3PO_4$ catalyst. 8.6 grams—except in Example IX where 6.0 grams was used—of a mixture containing, on a mole percent basis, 4-t-butylether-n-butan-1-ol and 3-t-butylether-2-methylpro-

TABLE 1

EXAMPLE I

Silica-Alumina[1] Catalyzed De-alkylation of 4-t-butylether-n-butan-1-ol at 120° C.

| Time/hr | THF[2] | t-butanol[2] | 1,4-di-t-butoxybutane[2] | 4-t-butylether-n-butan-1-ol[2] | 1,4-butanediol[2] | Av Rate[3] | Selectivity[4] | Conversion[5] |
|---|---|---|---|---|---|---|---|---|
| 1 | .95 | 1.05 | 5.3 | 63.4 | 29.2 | 39.7 | — | 29.2 |
| 2 | .67 | .73 | 5.6 | 52.6 | 40.4 | 27.4 | — | 40.4 |
| 3 | .38 | .42 | 4.7 | 46.4 | 48.0 | 21.9 | — | 48.0 |
| 4 | .52 | .60 | 3.7 | 36.9 | 58.2 | 19.9 | — | 58.2 |
| 5.5 | .95 | 1.05 | 3.1 | 28.8 | 66.1 | 16.4 | 98.6 | 66.1 |

[1] Grace-Davison grade 980-25 silica-alumina pellets crushed to a fine powder. Typical analysis of commercial Davidson silicon-alumina is set out hereafter in Example I - Table 1 Addendum.
[2] Mole percent.
[3] Av Rate = moles of 4-t-butylether-n-butan-1-ol converted to 1,4-butanediol/kg cat. × total elapsed reaction time period.
[4] Selectivity* = $\frac{\text{mole percent 1,4-butanediol}}{\text{mole percent 1,4-butanediol + mole percent THF}} \times 100$

*NOTE:
selectivity values at interim time periods are not reported since any THF contained in condensed isobutylene gas was only analyzed at conclusion of run.)

[5] Conversion = $\frac{\text{mole percent 1,4-butanediol}}{\text{mole percent 4-t-butylether-n-butan-1-ol originally charged}}$

Addendum

Grace-Davison — $SiO_2 \cdot Al_2O_3$ Typical Analysis

| Grade | 980-25 |
|---|---|
| CHEMICAL PROPERTIES | |
| (wt. %, Dry Basis @ 1750° F.) | 2.5 |
| Total Volatile @ 1750° F. | |
| Silica, $SiO_2$ | 74.5 |
| Alumina, $Al_2O_3$ | 25.0 |
| Sodium, $Na_2O$ | 0.05 |
| Sulfate, $SO_4$ | 0.30 |
| Iron, Fe | 0.03 |
| Calcium, CaO | 0.05 |
| Chlorine, Cl | <.01 |
| PHYSICAL | |
| Surface Area, $m^2/gm$ | 325 |
| Pore Volume, cc/gm | 0.45 |
| Packed Density, gm/cc | 0.73 |
| Avg. Crush Strength, lbs. | 15(3/16") |

Examples V–XI including the Second General Procedure illustrate attempts to de-alkylate—in the presence of other acidic substances—tertiary alkyletheralkanols. These examples are not a part of this invention and are furnished for the purpose of contrasting the efficacy of the acidic materials used as catalyst candidates with the efficacy of the silicaalumina catalysts used in Examples I–IV.

SECOND GENERAL PROCEDURE

A series of de-alkylation reactions were tried involving attempts to convert 4-t-butylether-n-butan-1-ol to pan-1-ol plus 0.20 grams of a catalyst candidate were blanketed with $N_2$ and heated in a 25 ml flask fitted with a reflux condenser and a magnetic stirrer. The liquid phase reaction product constituents were monitored employing standard V.P.C. techniques throughout the course of the reactions. A summary of the liquid phase reaction medium constituents, e.g. tetrahydrofuran (THF), 3-t-butylether-2-methyl-propan-1-ol, 2-methyl-1,3-propanediol, 4-t-butylether-n-butan-1-ol, and 1,4-butanediol correlated with elapsed reaction time period is reported in Examples V–XI.

TABLE 2

EXAMPLE II

Silica-Alumina[1] Catalyzed De-alkylation of 4-t-butylether-n-butan-1-ol at 125° C.

| Time/hr | THF[2] | t-butanol[2] | 1,4-di-t-butoxybutane[2] | 4-t-butylether-n-butan-1-ol[2] | 1,4-butanediol[2] | Av Rate[3] | Selectivity[4] | Conversion[5] |
|---|---|---|---|---|---|---|---|---|
| 1 | .52 | 1.6 | 6.3 | 54.9 | 36.6 | 50.1 | — | 36.6 |
| 2 | .67 | 1.5 | 4.5 | 36.6 | 56.7 | 38.8 | — | 56.7 |
| 3 | .55 | 1.2 | 4.2 | 31.4 | 62.6 | 28.6 | — | 62.6 |
| 4 | .48 | 1.2 | 3.3 | 25.4 | 69.7 | 23.9 | 98.5[6] | 69.7 |

Footnotes [1], [2], [3], [4] and [5] = same as in Example I - Table 1.
[6] = total THF 0.48 (liq. phase) + 0.57 (gas phase) = 1.05 mole %

TABLE 3

EXAMPLE III
Silica-Alumina[1] Catalyzed De-alkylation of 4-t-butylether-n-butan-1-ol at 130° C.

| Time/hr | THF[2] | 1,4-di-t-butoxybutane[2] | 4-t-butylether-n-butan-1-ol | 1,4-butanediol | Av Rate[3] | Selectivity[4] | Conversion[5] |
|---|---|---|---|---|---|---|---|
| 1 | 1.2 | 5.0 | 40.9 | 53.4 | 73.1 | — | 53.4 |
| 2 | 1.7 | 3.1 | 26.9 | 68.3 | 46.7 | — | 68.3 |
| 3 | 2.0 | 1.7 | 19.0 | 77.3 | 35.3 | — | 77.3 |
| 4 | 2.4 | 0.7 | 11.8 | 85.1 | 29.1 | — | 85.1 |
| 5.5 | 0.5 | 0.6 | 11.4 | 87.5 | 21.7 | 97.2[6] | 87.5 |

Footnotes [1], [2], [3], [4], and [5] = same as Example I - Table 1.
[6] = total THF 0.5 (liq. phase) + 2.0 (gas phase) = 2.5 mole %

TABLE 4

EXAMPLE IV
Silica-Alumina[1] Catalyzed De-alkylation of 4-t-butylether-n-butan-1-ol at 135° C.

| Time/hr | THF[2] | 1,4-di-t-butoxybutane[2] | 4-t-butylether-n-butan-1-ol[2] | 1,4-butanediol[2] | Av Rate[3] | Selectivity[4] | Conversion[5] |
|---|---|---|---|---|---|---|---|
| 0.5 | 0.7 | 5.9 | 49.9 | 43.5 | 119.2 | — | 43.5 |
| 1.0 | 0.9 | 4.4 | 39.3 | 60.5 | 82.9 | — | 60.5 |
| 1.5 | 2.4 | 3.5 | 27.7 | 66.4 | 60.6 | — | 66.4 |
| 2.0 | 2.0 | 2.4 | 22.4 | 73.2 | 50.1 | — | 73.2 |
| 3.0 | 2.6 | 1.1 | 12.0 | 84.3 | 38.5 | 95.4[6] | 84.23 |

Footnotes [1], [2], [3], [4], and [5] = same as Example I - Table 1.
[6] = total THF 2.6 (liq. phase) + 2.5 (gas phase) = 4.1 mole %

TABLE 5

EXAMPLES V–XI
Attempted Acid Catalyzed De-alkylation of Tertiary-Alkylether-Alkanols

| Ex. No. | Catalyst Candidate | Temperature Range | Time/hr | THF[1] | 3-t-butylether-2-methyl-propan-1-ol[1] | 2-methyl-1,3-propanediol[1] | 4-t-butylether-n-butan-1-ol[1] | 1,4-butanediol[1] | 1,4-butanediol Selectivity[2] | Conversion[3] |
|---|---|---|---|---|---|---|---|---|---|---|
| V | SiO$_2$ | 190°–192° C. | 0 | — | 13.8 | — | 81.7 | — | — | — |
|   |   |   | 2.5 | 0 | 13.8 | 0 | 81.7 | 0 | — | — |
| VI | Al$_2$O$_3$ | 172°–175° C. | 0 | — | 13.8 | — | 81.7 | — | — | — |
|   |   |   | 5.5 | 1.3 | 13.8 | trace | 78.6 | trace | n.d.[4] | trace |
| VII | MgO | 192°–195° C. | 0 | 0 | 16.2 | — | 74.2 | — | — | — |
|   |   |   | 3 | trace | 16.2 | trace | 74.2 | trace | n.d.[4] | trace |
| VIII | WO$_3$ . Al$_2$O$_3$ | 171° C. | — | — | 16.2 | — | 74.2 | — | — | — |
|   |   |   | 4.5 | trace | 15.3 | 0.92 | 70.6 | 3.60 | n.d.[4] | trace |
| IX | Acidic Clay | 95° C. | 0 | — | 13.9 | — | 86.1 | — | — | — |
|   |   |   | 6.5 | 9.8 | 0.15 | 14.2 | 0.9 | 75.1 | 88.5 | 87.2 |
| X | Acid Ion Exchange Resin | 95° C. | 0 | — | 13.6 | — | 86.4 | — | — | — |
|   |   |   | 9 | 30.5 | 6.4 | 8.2 | 24.1 | 30.8 | 50.2 | 35.7 |
| XI | Aq . H$_3$PO$_4$ | 145° C. | 0 | — | 13.6 | — | 86.4 | — | — | — |
|   |   |   | 5 | 12.1 | 0.1 | 12.9 | 0.4 | 74.5 | 86.0 | 86.2 |

[1]Mole percent.

[2]Selectivity* = $\dfrac{\text{mole percent 1,4-butanediol}}{\text{mole percent 1,4-butanediol + mole percent THF}} \times 100$

[3]Conversion = $\dfrac{\text{mole percent 1,4-butanediol}}{\text{mole percent 4-t-butylether-n-butan-1-ol originally charged}}$

*(NOTE no analysis of isobutylene effluent for trace amounts of other constituents.)

A brief description of the catalyst candidates of Examples V–X including their commercial sources, is set out in the following Table 5 Addendum:

| Example No. | Catalyst Candidate Description - Table 5 Addendum | |
|---|---|---|
| V | SiO$_2$ | J.T. Baker Co. - Silicic Acid, 88% SiO$_2$ . 12% H$_2$O |
| VI | Al$_2$O$_3$ | Alcoa-Activated Alumina |
| VII | MgO | Fisher-Magnesium Oxide, Certified Reagent Grade |
| VIII | WO$_3$ . Al$_2$O$_3$ | Harshaw Tungsten Oxide-W-0801 90% WO$_3$ . 10% Al$_2$O$_3$ |
| IX | Acidic Clay | Girdler KSF Montmorillonite Clay - a natural SiO$_2$ . Al$_2$O$_3$ clay treated with H$_2$SO$_4$ |
| X | Acid Ion Exchange Resin | Dow Chemical Co. Dowex(TM) 50WX8 a strongly acidic sulfonated polystyrene resin |

In general, the utility of this process provides for the de-alkylation of a tertiary-alkylether-alkanol of Formula (I) to form 1,4-alkanediols while at least 60, preferably 75–80, mole percent of tertiary-alkylether-alkanol is de-alkylated to form 1,4-alkanediols while the minimum ultimate selectivity of the process provides a 1,4-alkanediol/1,4-alkanediol plus cyclic ether product selectivity of at least about 95 percent.

The expression tertiary-alkylether-alkanol as used herein generically describes aliphatic and cycloaliphatic hydroxyethers commonly referred to as tertiary-alkoxy-alkanols, tertiary-cycloalkoxy-alkanols and tertiary-alkcycloalkoxy-alkanols. Illustratively as used herein the expressions:

tertiary-alkylether-alkanol also means tertiary-alkoxy-alkanol 4-t-butylether-n-butan-1-ol also means 4-t-butoxy-n-butan-1-ol 3-t-butylether-2-methyl-propan-1-ol also means 3-t-butoxy-2-methylpropan-1-ol Accordingly, as will be apparent to those skilled in the art, either of the above forms of chemical nomenclature can be used interchangeably throughout the specification as well as the claims.

We claim:

1. A de-alkylation process which comprises contacting a tertiary alkylether-alkanol with an acidic solid silica-alumina mixed oxide whereby alkanediols are formed in substantial absence of cyclic ethers.

2. The claim 1 process carried out at a temperature of from about 100° to 140° C.

3. The claim 2 process where the alkanediol conversion is equal to or greater than about 60 percent.

4. The claim 3 process where at least a portion of the tertiary-alkylether-alkanol is a 4-t-butylether-n-butan-1-ol.

5. The claim 4 process where the 4-t-butylether-n-butan-1-ol is the predominant tertiary-alkylether-alkanol feedstock.

6. The claim 3 process wherein the temperature is within the range of from about 125° to 135° C.

7. The claim 5 process where at least about 80% of the tertiary-alkylether-alkanol is converted to an alkanediol.

8. The claim 7 process where at least about 80% of 4-t-butylether-n-butan-1-ol is converted to 1,4-butanediol.

9. A de-alkylation process which comprises contacting (1) a tertiary-alkylether-alkanol of the formula:

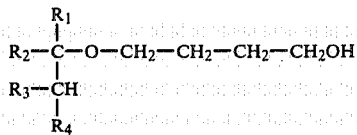

wherein independently, $R_1$ and $R_2$ each represent a $C_{1-4}$ alkyl, $R_3$ and $R_4$ each represent a hydrogen or a $C_{1-3}$ alkyl and optionally, where $R_1$ represents a $C_{1-4}$ alkyl, $R_2$ and $R_3$ conjointly with the two carbon atoms to which they are directly bonded in the above formula form a 5- or 6-membered cycloaliphatic ring, and $C_4$ represents hydrogen or a $C_{1-3}$ alkyl, with (2) an acidic solid silica-alumina mixed oxide at (3) a temperature of from about 100° to 140° C. whereby alkanediols are formed in the substantial absence of cyclic ethers, at least 60 percent of the tertiary-alkylether-alkanol is converted to an alkanediol and the minimum ultimate alkanediol selectivity is at least about 95%.

10. The claim 9 process which comprises contacting (1) a tertiary-alkylether-alkanol containing primarily 4-t-butylether-n-butan-1-ol with (2) acidic silica-alumina at (3) a temperature of from about 125° to 135° C., whereby 1,4-butanediol is formed in the substantial absence of tetrahydrofuran, at least 80% of the 4-t-butylether-n-butan-1-ol is converted to 1,4-butanediol and the minimum ultimate butanediol selectivity is at least about 97%.

* * * * *